United States Patent [19]

Otsuka et al.

[11] Patent Number: 4,695,631
[45] Date of Patent: Sep. 22, 1987

[54] PROCESS FOR THE PREPARATION OF ENAMINES OR IMINES

[75] Inventors: Seinosuke Otsuka; Kazuhide Tani, both of Hyogo; Tsuneaki Yamagata, Osaka; Susumu Akutagawa, Kanagawa; Hidenori Kumobayashi, Kanagawa; Misao Yagi, Kanagawa, all of Japan

[73] Assignee: Takasago Perfumery Co., Ltd., Tokyo, Japan

[21] Appl. No.: 393,982

[22] Filed: Jun. 30, 1982

[30] Foreign Application Priority Data

Jun. 30, 1981 [JP] Japan .................................. 56-102039

[51] Int. Cl.[4] ..................... C07C 87/24; C07D 295/02
[52] U.S. Cl. ................................... 544/170; 544/173; 544/178; 546/184; 546/192; 546/240; 546/248; 548/400; 548/574; 548/575; 548/578; 564/248; 564/355; 564/383; 564/454; 564/503; 564/509
[58] Field of Search ............... 564/509, 248, 278, 444, 564/508, 355, 383, 354, 503, 12, 15, 86; 548/400, 570, 574, 575, 578; 544/178, 177, 170, 173; 546/184, 248, 192, 240, 248

[56] References Cited

U.S. PATENT DOCUMENTS 4,137,417  1/1979  Hazama ............................. 560/22 X
4,234,484 11/1980  Mitzlaff et al. ........................ 548/531

OTHER PUBLICATIONS

Stille, et al.; C.A., 93 (1980), 93:7642q.
Oswald, C.A., 94 (1981), 94:157091u.
Tani, et al.; C.A., 97 (1982), 97:109322k.
Tani, et al.; C.A., 97 (1982), 97:145028c.
Smith, "The Chemistry of Open-Chain Organic Nitrogen Compounds", vol. 1 (1965), pp. 329–336; W. A. Benjamin, Inc. N.Y.
Houlen-Weyl, "Methoden Der Organischen Chemie", Stickstoff Verbendungen II, Band XI/I (1957), pp. 170–182, Georg Thieme Verlag, Stuttgart.
Sauer, et al.; Chem. Ber, 102 (1969), pp. 1917–1927.
Satoh, et al.; Chem. Lett. (1977), pp. 1465–1466.

Abstract of Japan Kokai No. 54-5906 (1979).
Abstract of Japan Kokai No. 54-5907 (1979).
Abstract of Japan Kokai No. 55-162730 (1980).

*Primary Examiner*—Joseph Paul Brust
*Attorney, Agent, or Firm*—Sughrue, Mion, Zinn, Macpeak, and Seas

[57] ABSTRACT

A process for the preparation of enamines or imines by isomerization of allylamine derivatives is described. Allylamine derivatives represented by formula (I):

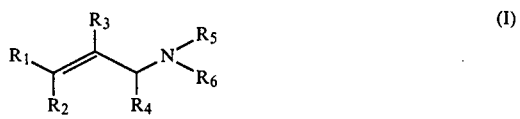

are isomerized using as a catalyst a rhodium complex represented by formula (IV):

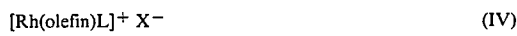

to form enamines or imines represented by, respectively, formula (II) or formula (III):

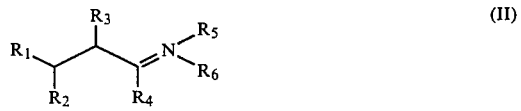

or

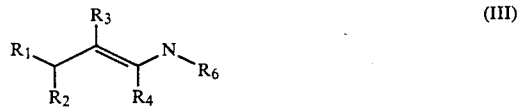

All of the symbols in the above formulae are as described. These enamines or imines are useful intermediates for the preparation of a number of organic compounds.

1 Claim, No Drawings

PROCESS FOR THE PREPARATION OF ENAMINES OR IMINES

FIELD OF THE INVENTION

The present invention relates to a process for the preparation of enamines or imines represented by, respectively, formula (II) or formula (III) as later specified.

BACKGROUND OF THE INVENTION

It is known that enamines or imines can be hydrolyzed quantitatively by, for example, dilute acids to form aldehydes or ketones, which aldehydes or ketones can be used to synthesize terpene compounds which are useful as, for example, flavor components or drugs such as vitamins. Thus, they are very important intermediates.

Known methods for the preparation of enamines or imines by the isomerization of allylamine derivatives include a method in which strong bases are used as catalysts (H. Sauer et al., *Chem. Ber.*, 102, 1917 (1969)), a method in which metal oxides are used as catalysts (Tanable et al., *Chem. Lett.*, 1465 (1977)), a method in which cobalt complexes are used as catalysts (Japanese Patent Application (OPI) Nos. 5906/79 and 5907/79 (the term "OPI" as used herein refers to a "published unexamined Japanese patent application")), and a method in which palladium complexes are used as catalysts (Japanese Patent Application (OPI) No. 162730/80).

As a result of extensive investigations on catalysts for use in such isomerization, it has been found that rhodium complexes permit isomerization of allylamine derivatives into enamines or imines in high yield.

SUMMARY OF THE INVENTION

The object of the invention is to provide a process for the preparation of enamines or imines represented by, respectively, formula (II) or formula (III) given hereafter by isomerization of allylamine derivatives represented by formula (I) given hereafter.

The present invention, therefore, relates to a process for producing enamines or imines represented by, respectively, formula (II) or formula (III):

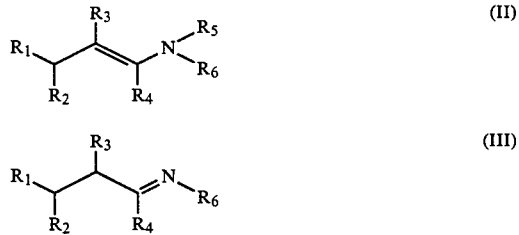

(all symbols are hereafter identified) by the isomerization of allylamine derivatives represented by formula (I):

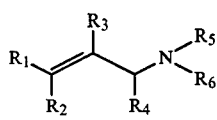

by the use of rhodium complexes represented by formula (IV):

$$[Rh(olefin)L]^{\oplus} X^{\ominus} \qquad (IV)$$

(all symbols are hereafter identified).

DETAILED DESCRIPTION OF THE INVENTION

The starting materials for use in the process of the invention are the allylamine derivatives represented by formula (I), wherein $R_1$, $R_2$, $R_3$ and $R_4$ are each hydrogen, an alkyl or alkenyl group, both of which may contain from 1 to 12 carbon atoms, or an aryl group; $R_1$ may be substituted by one hydroxy group; $R_5$ is hydrogen, or an alkyl or cycloalkyl group, both of which may contain from 1 to 8 carbon atoms; $R_6$ is an alkyl or cycloalkyl group, both of which may contain from 1 to 8 carbon atoms; or $R_5$ and $R_6$ may combine together in combination with the adjacent nitrogen atom to form a 5- or 6-membered ring, or a 6-membered ring containing an oxygen atom.

Examples of suitable allylamine derivatives are propene-2-yl-dimethylamine, 2-methyl-propene-2-yl-diethylamine, neryldiethylamine, geranyldiethylamine, 7-hydroxyneryldiethylamine, 7-hydroxygeranyldiethylamine, geranyl-cyclohexylamine, 1,3-dimethyl-butene-2-yl-dimethylamine, 3-phenyl-butene-2-yl-dimethylamine, 3-phenyl-butene-2-yl-diethylamine, 3,7,11-trimethyl-dodeca2,6,10-trienyldiethylamine(farnesyl-diethylamine), 2-methyl-propene-2-yl-pyrrolidine, hydroxygeranylmethylcyclohexylamine, neryl-di-n-butylamine, geranyl-di(2-ethylhexyl)amine, geranyl-di-sec-butylamine, and farnesyl-tert-butylamine.

These compounds are all commercially available or easily synthesized. Of these compounds, geranylamine derivatives and nerylamine derivatives are easily prepared by, for example, a method in which geranyl chloride or neryl chloride is prepared from geraniol or nerol by the use of phosphorus pentachloride and, thereafter, are reacted with amine lithium compounds derived from amine compounds and butyl lithium, or a method comprising teromerization of myrcene or isoprene with primary or secondary amines, catalyzed by an alkali metal compound (see, for example, K. Takabe et al., *Tetrahedron Letter*, 4009 (1972)).

The rhodium complexes for use in the invention are represented by formula (IV), wherein the symbol "olefin" indicates ethylene, 1,3-butadiene, norbornadiene, or cycloocta-1,5-diene; X indicates $ClO_4$, $BF_4$, or $PF_6$; and L indicates two mondentate triarylphosphines, or bidentate tri-valent phosphorus compound derivatives represented by formula (V):

$$(Aryl)_2-P-Y-P-(aryl)_2 \qquad (V)$$

where Y is $-(CH_2)_3-$, $-(CH_2)_5-$,

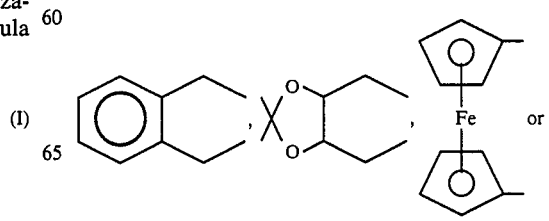

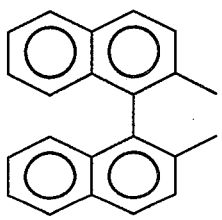

These rhodium complexes can be easily synthesized by the methods described in R. Richard et al., *J. Am. Chem. Soc.*, 93, 2397 (1971), *Shin Jikken Kagaku Koza*, Vol. 12, page 193, Maruzen Co., Ltd. (Tokyo), and H. Takaya et al., *J. Am. Chem. Soc.*, 102, 7932-4 (1980).

Some rhodium complexes have been isolated as crystals, and their chemical structures have been analyzed (see A. Miyashita et al., *J. Am. Chem. Soc.*, 102, 7932 (1980)). Such rhodium complexes isolated as crystals and "in situ" prepared rhodium complexes (e.g., described in *J.A.C.S.*, 94, 6433 (1972) by H. B. Kagan) can be used in the isomerization reaction of this invention.

The rhodium complexes of the invention can be prepared from mono-valent rhodium-olefin complexes, about 2 moles of monodentate ligands or about 1 mole of bidentate ligands per mole of the mono-valent rhodium-olefin complex, and about 1 mole of a salt containing a negative group per mole of the mono-valent rhodium-olefin complex.

Mono-valent rhodium-olefin complexes as used herein can be easily prepared by reacting rhodium trichloride with an olefin(s) in a solvent, e.g., methanol or ethanol. When ethylene is used as the olefin, there is prepared di-μ-chlorotetra(η-ethylene)dirhodium (I) according to the following reaction:

$$2RhCl_3 \cdot 3H_2O + 2H_2O + 6C_2H_4 \rightarrow [RhCl(C_2H_4)_2]_2 + 2CH_3CHO + 4HCl$$

Olefins which can be used in the preparation of the present rhodium complex catalysts include, in addition to ethylene, 1,3-butadiene, norbornadiene, and cycloocta-1,5-diene (hereinafter referred to as "COD"). They are used in the form of the corresponding monovalent rhodium complex to prepare the rhodium complex catalysts of the invention.

Monodentate ligands which can be used in the preparation of the present rhodium complex catalysts include triphenyl phosphine, tri-o-tolyl phosphine, and diphenyl β-naphthyl phosphine.

Bidentate ligands which can be used in the preparation of the present rhodium complex catalysts include the following compounds:

(o-Tol)$_2$P(CH$_2$)$_4$P(o-Tol)$_2$:  Bis(1,4-di-ortho-tolylphosphino)-butane;

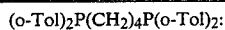 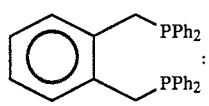  [bis(α,α'-diphenylphosphino)-ortho-xylylene];

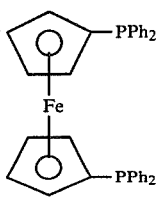  [1,1'-bis(diphenylphosphino)-ferrocene];

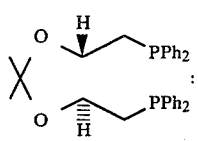  [2,3-o-isopropylidene-2,3-dihydroxy-1,4-bis(diphenylphosphino)-butane];

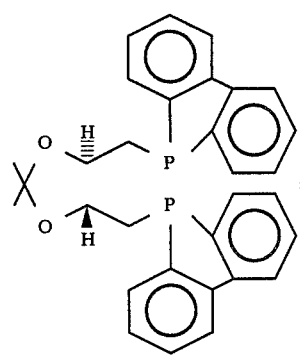  [2,3-o-isopropylidene-2,3-dihydroxy-1,4-bis(dibenzo-phospholyl)-butane];

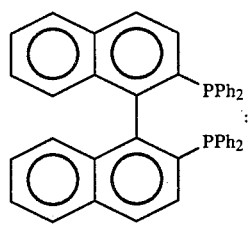  [2,2'-bis(diphenylphosphino)-1,1'-binaphthyl]; and

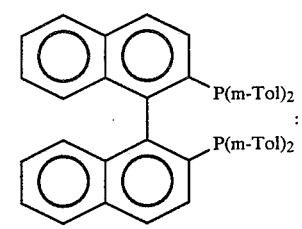  [2,2'-bis(di-meta-tolyl-phosphino)-1,1'-binaphthyl].

Salts containing a negative group which can be used in the preparation of the present rhodium complex catalysts include sodium perchlorate, magnesium perchlorate, silver perchlorate, sodium borofluoride, silver borofluoride, and potassium hexafluorophosphate. These salts are used to introduce the corresponding negative group into the rhodium complexes.

Preparation of a rhodium complex will hereinafter be explained in detail.

A mixture of 0.0616 g (0.25 millimole) of [Rh(COD)Cl]$_2$, 0.078 g (0.375 millimole) of silver perchlorate, and 0.17 g (0.275 millimole) of 2,2'-bis(diphenylphosphino)-1,1'-binaphthyl (hereinafter referred to as "BINAP") was dissolved in 10 ml of tetrahydrofuran and stirred at 20° C. for 1 hour in a nitrogen atmosphere. At the end of this period, the silver chloride thus formed and excess of silver perchlorate were filtered off. The filtrate thus obtained is used as a catalyst in the isomerization reaction of the invention.

In the preparation of the rhodium complex catalysts of the invention, the optimum method and conditions are chosen depending on the type of the reagent used, the molar ratio, the type of the solvent, etc.

The isomerization reaction of the invention is achieved by adding a rhodium complex to the allylamine derivative in a proportion of 1/2,000 to 1/6,000 mole per mole of the allylamine derivative, and then maintaining the resulting mixture at a temperature of from 20° to 150° C. for a period of from 2 to 10 hours.

This isomerization reaction does not always require a solvent. In order to dissolve the rhodium complex and to make the reaction proceed smoothly, it may be advantageous to use a solvent, however. Solvents which can be used usually from 0.3 to 2 times per raw material amine for that purpose include aromatic hydrocarbons such as benzene, toluene, and xylene; ethers such as tetrahydrofuran, diethylene glycol dimethyl ether, and 1,3-dioxane; halides such as dichloromethane and chlorobenzene; alcohols such as methanol and 2-ethyl-1-hexanol; and ketones such as acetone and methyl ethyl ketone.

After the reaction is completed, the solvent is recovered in a conventional manner and, thereafter, the desired enamine or imine is obtained by distillation. When there are used, as starting materials, allylamine derivatives represented by formula (I) wherein $R_5$ is a substituent other than hydrogen, enamines are formed, whereas when $R_5$ is hydrogen, imines are formed, and hydrotropy tautomerism occurs, forming imines in a stable form.

When an asymmetric reaction is carried out in the isomerization reaction of this invention, if there is used a rhodium complex where its ligand, i.e., L of formula (IV), is an optically active compound, an enamine or imine having optical activity can be prepared. For example, when an optically active tri-valent phosphorus compound having plane asymmetry (see the Japanese version (translated by Shimamura et al.) of E. L. Eliel, *Stereochemistry of Carbon Compounds*, page 180, Tokyo Kagakudojin (1965)), e.g., BINAP represented by the following formula:

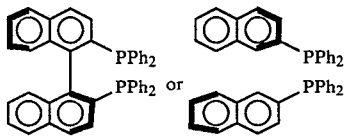

(wherein the heavy line indicates plane asymmetry) is used, "enantiomer excess" (optical yield) reaching 95% is obtained. That is, the isomerization of neryldiethylamine is performed by the use of a rhodium complex comprising an optically active tri-valent phosphorus compound to prepare an enamine, and by hydrolyzing the thus-prepared enamine with dilute sulfuric acid, there can be prepared optically active citronellal having an optical purity of 95% at a high yield of 93%. When it is considered that the optical purity of citronellal contained in natural citronella oil is about 85%, it can be seen that the above results are excellent. Optically active citronellal is used as an intermediate for the synthesis of l-menthol.

The process of the invention enables one to prepare enamines or imines in high yield by isomerization of allylamine derivatives and, thus, it can be widely used and is useful not only in the preparation of terpenoids but also in the preparation of general organic compounds.

Unless otherwise indicated, in the following Examples all temperatures are at room temperature. Further, unless otherwise indicated, all pressures were at atmospheric pressure except, of course, when procesing was in a sealed vessel, in which case pressure was autogenous.

The following Examples are given to illustrate the invention in greater detail.

EXAMPLE 1

A mixture of 61.5 mg [Rh(COD)Cl]$_2$ and 171 mg (+)BINAP[[$\alpha$]$_D^{23}$+227°($_{benzene}C=0.35$)] was placed in a flask equipped with a three-way cock under a stream of argon and, after the addition of 25 ml of tetrahydrofuran with stirring, it was further stirred for 10 minutes. Then, 2.5 ml of a tetrahydrofuran solution containing 51.8 mg of AgClO$_4$ was added thereto, and the resulting mixture was stirred at room temperature for 30 minutes. The silver chloride thus formed was removed by filtration, and the filtrate was used as a catalyst solution.

A 100 ml pressure bomb was purged with nitrogen, and after the introduction of 20 ml of tetrahydrofuran, 5 ml of the above-prepared rhodium complex catalyst solution and 26 g of neryldiethylamine, it was sealed and heated at 100° C. for 17 hours while stirring to perform isomerization.

After the reaction was completed, the bomb was opened, the tetrahydrofuran was distilled off, and the resulting reaction concentrate was distilled to yield 24.8 g of a fraction having a boiling point of 75° to 80° C./1 mmHg.

It was confirmed from GLC and NMR analyses and measurement of optical rotation that the fraction was d-citronellal enamine.

Optical Rotation: [$\alpha$]$_D^{23}$−73°[C=5.3, n-hexane]

NMR (CDCl$_3$):

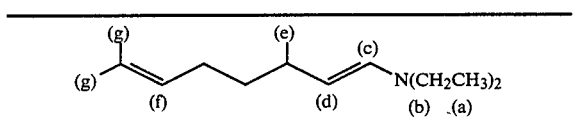

(a) δ 1.0(t, 6H, CH$_2$—C$\underline{H}_3$), (e) δ 1.0 (d, 3H, CH—C$\underline{H}_3$), (g) δ 1.6 (d, 6H, =C$\diagdown_{\underline{CH}_3}^{CH_3}$), (b) δ 2.85 (q, 4H, N—C$\underline{H}_2$—CH$_3$), (c) δ 5.68 (d, 1H, =$\diagup_{\underline{H}}^{N}$), (d) δ 3.85 (q, 1H, 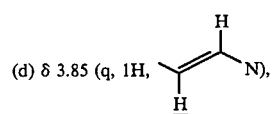

(f) δ 5.05 (t, 1H, $\diagup$=$\diagdown_{\underline{H}}$ )

-continued

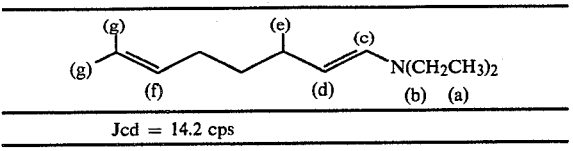

Jcd = 14.2 cps

Subsequently, the thus-prepared citronella enamine was poured into 300 ml of water and colled with ice, and 8 g of acetic acid was dropwise added thereto at a temperature of from 5° to 10° C. while stirring. After the dropwise addition was completed, the resulting mixture was stirred for 10 minutes. The reaction solution was then subjected to extraction using 200 ml of n-hexane. The extract thus-obtained was washed with water and subsequently with a saturated aqueous solution of sodium carbonate, and it was then dried over anhydrous magnesium sulfate. The n-hexane was distilled off, and the residue was subjected to distillation to yield 16.8 g of a fraction having a boiling point of from 53° to 55° C./1 mmHg.

Gas chromatographic analysis showed that the above prepared fraction was composed of 97% of citronellal. The optical rotation thereof was measured at a purity of 100%, which was achieved by gas chromatographic separation and found to be $[\alpha]_D^{23} +15.5°$ (neat).

Comparison with the absolute optical rotation $[\alpha]_D^{23} +16.5°$ (neat) described in B. Budley et al., *Perfume and Essential Oil Record*, 365–366 (1968), confirmed that the citronellal prepared in this example was d-citronellal having an optical purity of 94%.

EXAMPLE 2

A 200 ml pressure bomb was purged with nitrogen, and, after the introduction of 50 ml of tetrahydrofuran, 12.5 ml of the rhodium complex catalyst solution prepared in Example 1 and 52 g of geranyldiethylamine, it was sealed and heated at 100° C. for 17 hours to perform isomerization.

After the reaction was completed, the bomb was opened, the tetrahydrofuran was distilled off, and the residue was subjected to distillation to yield 49.2 g of a fraction having a boiling point of 75° to 79° C./1 mmHg.

GLC analysis and measurement of the optical rotation thereof confirmed that the fraction was l-citronellal enamine having an optical rotation of $[\alpha]_D^{23} +74.5°$ (C=5.01, n-hexane).

Subsequently, the thus prepared l-citronellal enamine was poured into 300 ml of water, and then 15 g of acetic acid was dropwise added at a temperature of from 5° to 10° C. while cooling with ice and stirring. The resulting mixture was stirred for 15 minutes to perform hydrolysis of the enamine and, thereafter, the reaction solution was subjected three times to extraction using 100 ml of n-hexane. The thus obtained extract was treated in the same manner as in Example 1 to yield 33 g of a fraction having a boiling point of from 54° to 55° C.

GLC analysis showed that the fraction was composed of 97% of citronellal. At a purity of 100%, achieved by gas chromatographic separation, the optical rotation was measured and found to be $[\alpha]_D^{23} -15.8°$ (neat). This showed that the citronellal prepared in this example was l-citronellal having an optical rotation of 96%.

EXAMPLE 3

While flowing nitrogen through a 400 ml pressure vessel there was placed therein 229 mg (0.25 millimole) of a rhodium complex, [Rh(R)—(+)BINAP) (norbornadiene)]+ClO4− (prepared by the method described in H. Takaya et al., *J. Am. Chem. Soc.*, 102, 7932–4 (1980)), 70 ml of tetrahydrofuran was then added with stirring to dissolve therein the rhodium complex and subsequently 114 g of hydroxyneryldiethylamine was added thereto. The vessel was then sealed and heated at 100° C. for 15 hours to perform isomerization.

After the reaction was completed, the vessel was opened, the tetrahydrofuran was recovered by distillation, and the residue was then subjected to distillation to yield 112 g of a fraction having a boiling point of 105° to 110° C/1 mmHg.

GLC analysis and NMR analysis confirmed that the fraction was hydroxycitronellal enamine having a purity of 98%.

NMR (CDCl₃):

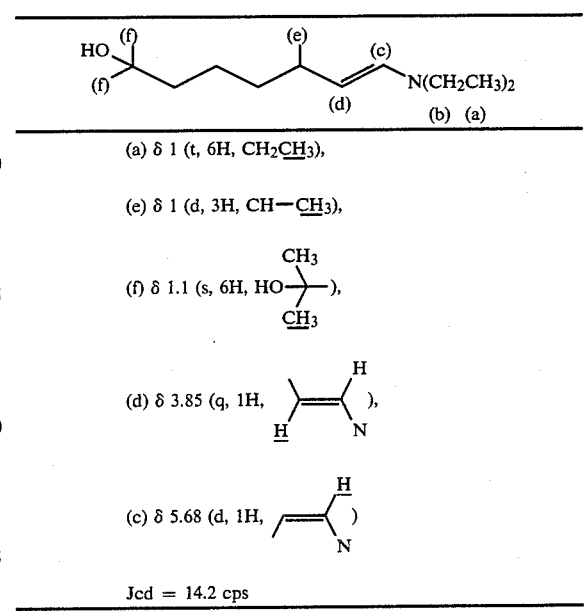

Jcd = 14.2 cps

The thus prepared hydroxycitronellal enamine was treated in the same manner as in Example 1, and the resulting hydrolyzed solution was extracted three times with 200 ml of benzene each time. The extracts were combined, washed with 300 ml of a 5% aqueous solution of sulfuric acid, twice with water, and finally, with a saturated aqueous solution of sodium carbonate and dried over anhydrous magnesium sulfate. The benzene was distilled off, and the residue subjected to distillation to yield 73 g of a fraction having a boiling point of from 85° to 90° C./2 mmHg.

GLC analysis showed that the fraction was hydroxycitronellal having a purity of 99.9%, and the optical rotation was $[\alpha]_D^{23} +11°$ (C=20, benzene), confirming that it was d-hydroxycitronellal.

The optical rotation of d-hydroxycitronellal as described in W. Skorianetz, H. Giger, and G. Ohloff, *Helvetica Chimica Acta.*, 54, 1797–1801 (1971), is $[\alpha]_D^{20} +10°$.

EXAMPLE 4

While flowing nitrogen through a 400 ml pressure vessel there was placed 229 mg of a rhodium complex, [Rh((S)—(—)BINAP)(norbornadiene)]+ClO4−, prepared in the same manner as in Example 3, and 60 ml of tetrahydrofuran was added thereto to dissolve the rhodium complex, forming a uniform solution thereof. After the addition of 112 g of hydroxygeranyldiethylamine to the uniform solution, the vessel was sealed and reaction performed by heating at 100° C. for 17 hours to yield 110 g of an enamine having a boiling point of from 105° to 108° C./1 mmHg.

Subsequently, the procedure of Example 3 was repeated to yield 70 g of a fraction having a boiling point of from 75° to 80° C./1 mmHg.

GLC analysis and measurement of optical rotation confirmed that the fraction was d-hydroxycitronellal having a purity of 99.95% and $[\alpha]_D^{24} + 12°$ (C=20, benzene).

example 5

To a mixture of 24.6 mg [Rh(COD)Cl]2 and

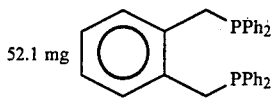

(bis(α,α'-diphenylphosphino)-orthoxylilene) was added 10 ml of tetrahydrofuran under a stream of nitrogen while stirring to prepare a uniform solution. Then, 20.8 mg of silver perchlorate was added to the uniform solution, and the resulting mixture was stirred at room temperature for 30 minutes. The precipitated silver chloride was filtered off, and the filtrate used as a catalyst solution.

In a 100 ml pressure vessel maintained under a stream of nitrogen were placed 20 ml of tetrahydrofuran, 10 ml of the catalyst solution as prepared above, and 12 g of 2(Z)6(E)-farnesyldiethylamine. The vessel was then sealed, and they were reacted at 100° C. for 18 horus. Distillation was performed to yield 10 g of an enamine having a boiling point of from 115° to 120° C./1 mmHg.

The thus prepared enamine was hydrolyzed using acetic acid and treated in the same manner as in Example 1 to yield 7.2 g of a fraction having a boiling point of from 95° to 100° C./1 mmHg.

GLC and NMR analyses showed that the fraction was 6(E)-3,7,11-trimethyl-6,11-dodecadien-1-al having a purity of 98%.

NMR (CDCl3):

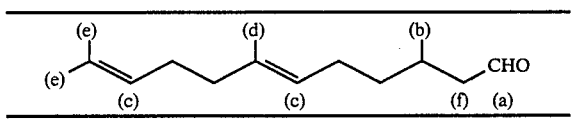

(b) δ 1.0 (d, 3H, CH—CH3), (e) δ 1.6 (d, 6H, =C<CH3/CH3), (d) δ 1.63 (s, 3H, )=<(/CH3),

-continued

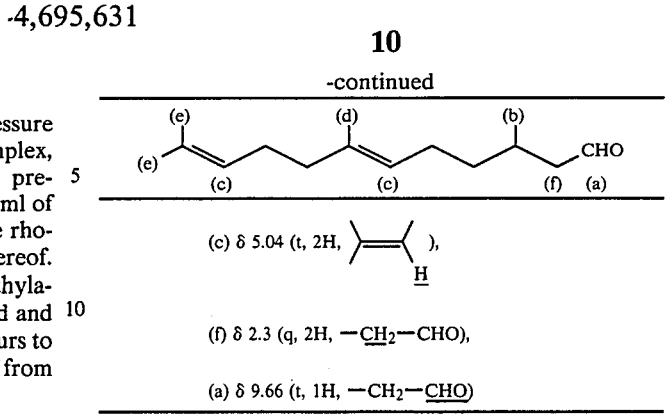

(c) δ 5.04 (t, 2H, )=<(/H ), (f) δ 2.3 (q, 2H, —CH2—CHO), (a) δ 9.66 (t, 1H, —CH2—CHO)

EXAMPLE 6

A rhodium complex catalyst, [Rh(COD)((R)—(+-)BINAP)]+ClO4−(0.028 g), which had been prepared in the same manner as in Example 1, was weighed and placed in a flask equipped with a three-way cock, into which was introduced 6 ml of tetrahydrofuran under a stream of argon to dissolve the catalyst. Additionally, 0.71 g of geranylcyclohexylamine was added thereto, and they were reacted at 40° C. for 23 hours.

After the reaction was completed, the tetrahydrofuran was recovered, and an oily fraction was distilled off under reduced pressure to yield 0.7 g of an oily material having a boiling point of 130° C./2 mmHg.

GLC and NMR analyses showed that the material was the cyclohexylimine of citronellal. The optical rotation was $[\alpha]_D^{23} - 6.04°$ (C=16.2, hexane). Compared with the optical rotation value given in the literature, the optical purity was determined to be 95.9%.

NMR (CDCl3):

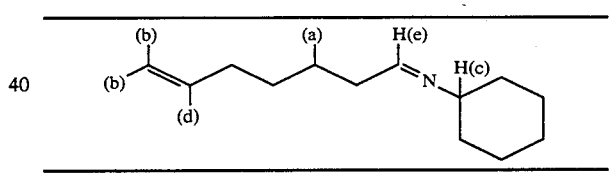

(a) δ 1.0 (d, 3H, CH—CH3), (b) δ 1.6 (d, 6H, =C<CH3/CH3), (c) δ 2.9 (m, 1H, N—C—H), (e) δ 5.2 (t, 1H, =CH—), (e) δ 7.6 (t, 1H, —N=CH—)

EXAMPLE 7

In a pressure bomb which had been purged with argon there was placed 0.28 g of a rhodium complex, [RH(COD)((R)—(+)BINAP)]+ClO4−, and 70 ml of tetrahydrofuran was added to dissolve the rhodium complex, forming a uniform solution. Subsequently, 5.3 g of 3-phenylbutene-2-yldimethylamine was added and the bomb was sealed and maintained at 60° C. for 48 hours to complete isomerization. After the reaction, the solvent was recovered by distillation, and the residue was subjected to distillation to yield 5 g of a fraction having a boiling point of from 117° to 120° C./2 mmHg.

GLC and NMR analyses showed that the fraction was 3-phenyl-butene-1-yldimethylamine.

NMR (CDCl₃):

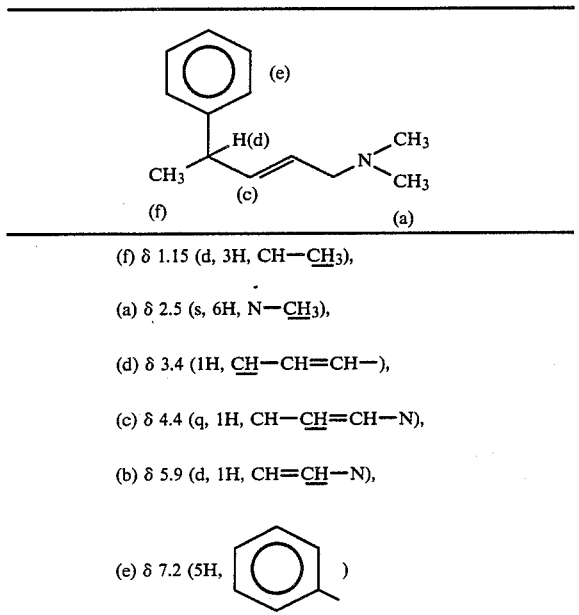

(f) δ 1.15 (d, 3H, CH—C$\underline{H}_3$), (a) δ 2.5 (s, 6H, N—C$\underline{H}_3$), (d) δ 3.4 (1H, C$\underline{H}$—CH=CH—), (c) δ 4.4 (q, 1H, CH—C$\underline{H}$=CH—N), (b) δ 5.9 (d, 1H, CH=C$\underline{H}$—N), (e) δ 7.2 (5H, ⌬ )

In order to determine the optical purity of the enamine prepared by the isomerization, the enamine was first converted into the corresponding aldehyde by the same procedure as in Example 1 and, thereafter, in accordance with the method described in:

(1) A. I. Pearl, *Journal of Organic Chemistry*, 12, 85 (1947);
(2) O. Schlindler, *Pharm. Acta. Helv.*, 20, 79 (1945): or
(3) E. Campaigne, *Organic Synthesis*, 33, 94 (1953), the aldehyde was converted into the corresponding carboxylic acid and its optical rotation was measured as: $[\alpha]_D^{26}$ −52.3° (C=2.4, benzene). Comparison with the optical rotation value $[\alpha]_D^{24}$ −58.5°, described in D. J. Cram, *J.A.C.S.*, 74, 2137 (1952), showed that the optical purity of the enamine prepared by the isomerization was 89.5%.

EXAMPLE 8

(−)-2,3-o-Isopropylidene-2,3-dihydroxy-1,4-bis(diortho-tolyphosphino)-butane (66.48 mg), which had been prepared by the method described in H. B. Kagan, *Journal of Organometal Chemistry*, 91, 105 (1975), and 24.6 mg [Rh(COD)Cl]₂ were placed in a 20 ml flask equipped with a three-way cock, which was then purged with nitrogen. Then, 10 ml of tetrahydrofuran was added thereto to form a uniform solution, and then 19.5 mg of silver borofluoride was added. The resulting mixture was stirred for 30 minutes. Silver chloride formed was removed by filtration to prepare a rhodium complex catalyst.

The thus prepared rhodium complex catalyst was transferred into a 100 ml pressure bomb which had been purged with nitrogen gas, and, after the introduction of 12.5 g of 2-methyl-propene-2-yl-pyrrolidine, the bomb was sealed. Isomerization was completed by stirring the mixture at 100° C. for 16 hours. After the reaction, the tetrahydrofuran was distilled off and, subsequently, 11 g of a fraction having a boiling point of from 130° to 132° C./760 mmHg was obtained by the distillation.

GLC and NMR analyses showed that the fraction was 2-methyl-propene-1-yl-pyrrolidine having a purity of 98%.

NMR (CDCl₃):

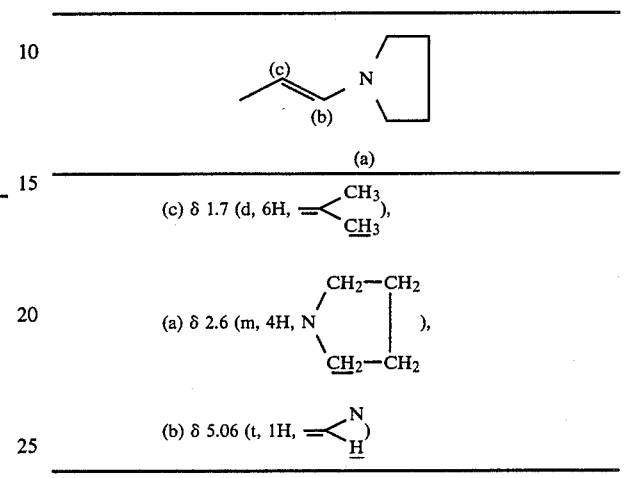

EXAMPLE 9

A rhodium complex catalyst solution (10 ml) prepared in the same manner as in Example 1 was placed in a 100 ml pressure bomb which had previously been purged with nitrogen gas. Then, 20 ml of tetrahydrofuran was added thereto, and, finally, 6.4 g of 1,3-dimethylbutene-2-yl-dimethylamine was added. They were reacted at 110° C. for 20 hours. After the reaction was completed, the tetrahydrofuran was distilled off, and 5.6 g of a fraction having a boiling point of from 117° to 120° C./760 mmHg was obtained by the distillation.

GLC and NMR analyses showed that the fraction was 1,3-dimethyl-butene-1-yl-dimethylamine having a purity of 95%.

NMR (CDCl₃):

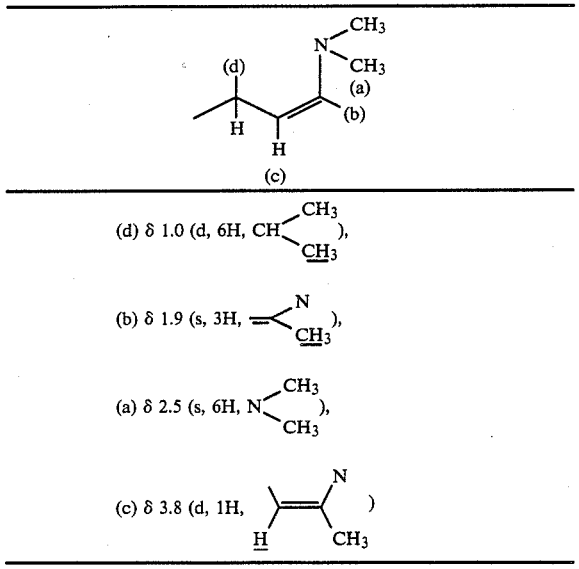

EXAMPLE 10

Chlorobis(1,3-butadiene)rhodium, RhCl(C₄H₆)₂ (61.5 mg), and 111 mg of triphenylphosphine were placed in a 50 ml flask equipped with a three-way cock, and, after the addition of 25 ml of tetrahydrofuran under a stream of nitrogen, they were stirred for 10 minutes. Thereafter, 2.5 ml of a tetrahydrofuran solution containing 46.0 mg of potassium hexafluorophosphate was added thereto, and the resulting mixture was stirred at 20° C. for 30 minutes. Potassium chloride thus formed was removed by filtration to provide a catalyst solution.

The thus prepared catalyst solution (2 ml) was added to 20 ml of a methanol solution containing 25 g of N-allyl morpholine in a 100 ml bomb, and, after purging with nitrogen gas, they were reacted by heating at 50° C. for 2 hours.

In order to confirm the isomerization reaction, the reaction solution prepared as above was subsequently dropwise added to 200 ml of a 5% aqueous solution of sulfuric acid. The resulting mixture was stirred and allowed to stand short time, an oily fraction was separated. GLC analysis showed that the oily fraction contained 7.5 g of acetaldehyde. Yield was 85.3% based on the weight of N-allylmorpholine.

EXAMPLE 11

A catalyst solution (2 ml) prepared in the same manner as in Example 1 was added to 30 ml of an acetone solution conftaining 31 g of N-3,3-dimethylallylpiperidine in a 100 ml autoclave, and, after purging with nitrogen gas, they were reacted by heating at 70° C. for 2 hours.

In order to confirm the isomerization reaction, the reaction solution prepared as above was subsequently dropwise added to 100 m of a 10% aqueous solution of sulfuric acid. The resulting mixture was stirred and allowed to stand short time, an oily fraction was separated. GLC analysis showed that the oily fraction was isovaleraldehyde (15.1 g) having a purity of 98%. Yield was 86.7% based on the weight of N-3,3-dimethylallyl-piperidine.

EXAMPLES 12 TO 15

In preparing a catalyst solution in the same manner as in Examples 1 to 11, the type of the ligand was changed.

A ligand as shown in the following Table (20 millimoles in the case of a monodentate ligand; 10 millimoles in the case of a bidentate ligand) was mixed with 10 millimoles of Rh(COD)Cl₂. To the resulting mixture was then added 10 millimoles of silver perchlorate in tetrahydrofuran. The silver chloride formed was removed by filtration, and the filtrate was used as a catalyst.

Neryldiethylamine was used as the allylamine derivative. With regard to the amount of the catalyst used, the ratio of neryldiethylamine to Rh was adjusted to 1,000/1 in molar ratio.

Reaction was performed at 100° C. for 5 hours. The reaction solution was subjected to GLC analysis, and the amount of enamine formed was calculated. The results are shown in the Table below.

TABLE

| Example | Ligand | Yield of Enamine (wt %) |
|---|---|---|
| 12 | Diphenyl-β-naphthylphosphine | 75 |
| 13 | (−)-2,3-o-Isopropylidene-2,3-dihydroxy-1,4-bis(diphenylphosphino)-butane | 62 |
| 14 | (+)-2,3-o-Isopropylidene-2,3-dihydroxy-1,4-bis(di-ortho-tolylphosphino)-butane | 77 |
| 15 | Bis(α,α-diphenylphosphino)-ortho-xylilene | 85 |
| 16 | 1,4-Bis(diphenylphosphino)-butane | 58 |
| 17 | 1,3-Bis(diphenylphosphino)-propane | 52 |
| 18 | 1,1′-Bis(diphenylphosphino)-ferrocene | 72 |

While the invention has been described in detail and with reference to specific embodiments thereof, it will be apparent to one skilled in the art that various changes and modifications can be made therein without departing from the spirit and scope thereof.

What is claimed is:

1. A process for preparing an enamine represented by formula (II):

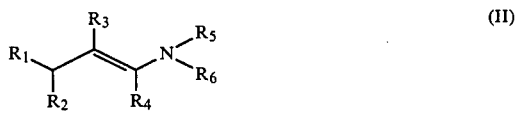

(II)

wherein R₁, R₂, R₃ and R₄ are each hydrogen, an alkyl group containing from 1 to 12 carbon atoms, an alkenyl group containing up to 12 carbon atoms, or a phenyl group, wherein R₁ may be substituted by one hydroxy group; R₅ is hydrogen, an alkyl group containing from 1 to 8 carbon atoms, or a cycloalkyl group containing from 6 to 8 carbon atoms; R₆ is an alkyl group containing from 1 to 8 carbon atoms or a cycloalkyl group containing from 6 to 8 carbon atoms; or R₅ and R₆ may combine together in combination with the adjacent nitrogen atom to form pyrrolidine, piperidine or morpholine; or an imine represented by formula (III):

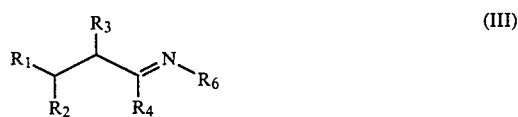

(III)

wherein R₁, R₂, R₃, R₄ and R₆ are the same as for formula (II), isomerizing an allylamine derivative represented by formula (I):

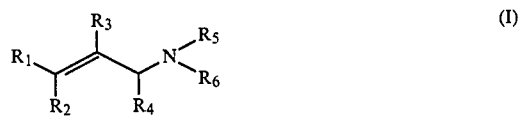

(I)

wherein R₁, R₂, R₃, R₄, R₅ and R₆ are the same as for formula (II), using as a catalyst a rhodium complex represented by formula (IV):

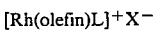

wherein olefin represents ethylene, 1,3-butadiene, norbornadiene or cycloocta-1,5-diene; X represents ClO₄, BF₄ or PF₆; and L represents two triarylphosphines wherein the aryl moiety is a phenyl, a tolyl or a naphthyl group or a tri-valent phosphorous compound derivative represented by formula (V):
(aryl)₂—P—Y—P—(aryl)₂     (V)
wherein the aryl moiety is a phenyl, an ortho-tolyl or a metal-tolyl group, or (aryl)₂ is a 2,2′-biphenyl group and Y represents -(CH₂)₃—, —(CH₂)₄—, —(CH₂)₅—,
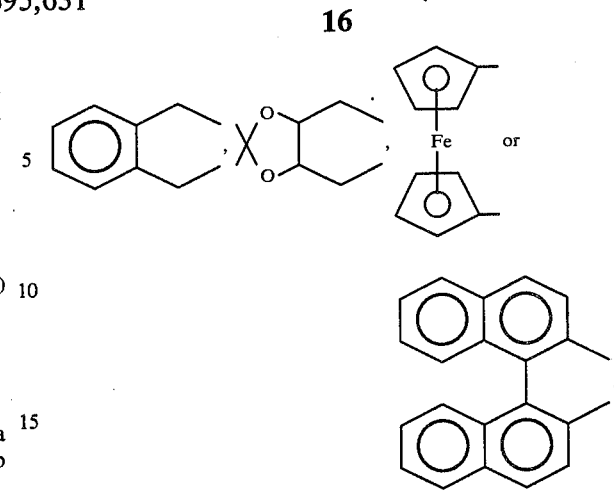
* * * * *